United States Patent [19]

Billings et al.

[11] Patent Number: 5,160,334
[45] Date of Patent: Nov. 3, 1992

[54] ELECTROSURGICAL GENERATOR AND SUCTION APPARATUS

[75] Inventors: R. Gail Billings, Holladay; William D. Wallace, Salt Lake City; Christopher A. Cutler, Centerville; B. Tod Cook, Sandy, all of Utah

[73] Assignee: Utah Medical Products, Inc., Midvale, Utah

[21] Appl. No.: 693,560

[22] Filed: Apr. 30, 1991

[51] Int. Cl.⁵ .............................................. A61B 17/39
[52] U.S. Cl. ...................................... 606/34; 606/38; 606/45; 606/49; 604/35
[58] Field of Search ............................ 606/34, 37–40, 606/42, 45, 46, 48–50; 604/35

[56] References Cited

U.S. PATENT DOCUMENTS

| | | | |
|---|---|---|---|
| 2,275,167 | 3/1942 | Bierman | 606/42 |
| 4,562,838 | 1/1986 | Walker | 604/35 X |
| 4,719,914 | 1/1988 | Johnson | 604/35 X |
| 5,035,695 | 7/1991 | Weber, Jr. et al. | 604/35 X |
| 5,071,418 | 12/1991 | Rosenbaum | 604/35 X |

FOREIGN PATENT DOCUMENTS 9003152  4/1990  World Int. Prop. O. ............ 606/46

OTHER PUBLICATIONS

Stackhouse Incorporation, Nov. 90-5M Product Catalog, "Laser Smoke Filtration Systems—Point One TM and the LFA-100 Systems and Accessories."

Birtcher Corporation Product Catalog, Mar. 1990, two pages, "The Model 774 Electrosurgery Generator."
Valleylab Product Catalog, 2 pages, "Valleylab generators: When performance counts, we've got the numbers."

Primary Examiner—Lee S. Cohen
Attorney, Agent, or Firm—Madson & Metcalf

[57] ABSTRACT

An electrosurgical unit which combines an electrosurgical power generator and a filtered smoke removal system into a single compact instrument comprising an electrosurgical generator module and a smoke removal module. The electrosurgical generator module is designed specifically to accommodate an electrosurgical tool during LEEP or LLETZ procedures. The electrosurgical generator module provides power to the electrosurgical tool at a predetermined level. The smoke removal module removes and filters smoke from the site of the electrosurgery. A switching circuitry activates the smoke removal module substantially simultaneous to the activation of the electrosurgical tool so that the smoke removal module is activated automatically whenever the electrosurgical tool is activated. The switching circuitry also delays the deactivation of the smoke removal module for a predetermined amount of time after the electrosurgical tool has been deactivated. The electrosurgical tool alternatively can be connected, concentrically or in parallel, to a smoke evacuation tube in communication with the smoke removal module.

30 Claims, 5 Drawing Sheets

ELECTROSURGICAL GENERATOR AND SUCTION APPARATUS

FIELD OF THE INVENTION

The present invention relates to an apparatus used for driving a tool during electrosurgical procedures, and more particularly to an electrosurgical generator with an integrated smoke evacuator for providing power for an electrosurgical tool while providing simultaneous smoke evacuation capability.

BACKGROUND OF THE INVENTION

In recent years there has developed an increased incidence of cervical intraepithelial neoplasia (CIN), i.e., sexually transmitted genital warts. Since the majority of cases occur in women of reproductive age who have not completed their families, conservative treatment has been advisable.

Management procedures using electrocoagulation, electrodiathermy, cryosurgery and laser surgery are accepted but each such procedure has drawbacks and all require considerable skill and experience. Cold knife and laser surgery typically require hospitalization and general anesthesia. Using these procedures, there are occasions when the practitioner will miss invasive cancers or inadvertently treat cancers with ablative therapy.

Recently, loop electrosurgical excision procedures (LEEP) and large loop excision of the transformation zone (LLETZ) using thin wire electrodes powered by an electrosurgical generator have been used to treat CIN. These electrosurgical techniques can be provided on an outpatient basis under either local or general anesthesia. Also, these electrosurgical techniques have the advantage over other destructive techniques in that the specimen excised is not destroyed, but preserved for examination histologically. Additionally, microinvasive and invasive disease can be excluded and the limits of the lesion are clearly defined.

In performing these electrosurgical techniques, the electrosurgical tool used is a loop. The loop is used with a monopolar generator (the "electrosurgical unit") which produces a number of waveforms for electrosurgical cutting and coagulation. In monopolar electrosurgery, a radio frequency current is passed through the body of the patient between an active electrode, where the current is very concentrated, and a disperse electrode, where the current is quite diffuse. The loop acts as the active electrode and is used as a cutting tool at the surgical site.

The loop comprises an insulated shaft connected to insulated extending arms to which a loop wire is attached. The loop is connected to and is controlled by either a hand switch or a foot switch connected to the electrosurgical unit. The dispersive electrode is applied to the patient's body at a site away from the surgical field. Its purpose is to complete the electrical circuit and disperse the current returning to the electrosurgical unit.

Electrosurgery results from the concentration of electrical energy in tissue of the patient to the point that local tissue is destroyed or modified. In electrosurgical cutting, the cells conducting the concentrated current are heated to where the water contained within the cells boils causing the cells to explode and release the resulting steam. In electrosurgical coagulation, cells near the surface exposed to the concentrated current are heated so that they dehydrate and shrink, rather than explode, thereby closing open vessels.

To obtain cutting with a minimal heating, the electrosurgical unit drives the small-wire loop with a continuous, unmodulated waveform. Cutting with shallow surface coagulation is obtained by modulating the cutting power source. This is known as a blended source. Typical electrosurgical units have a pure cut mode and multiple (usually three) blend modes. These blend modes use waveforms comprising bursts of radio frequency energy with smaller duty cycles causing greater coagulation activity and less cutting activity.

To obtain coagulation without cutting, typically an active electrode with larger cross section is used with the power source supplying an interrupted waveform. Two forms of coagulation are desiccation and fulguration.

Desiccation coagulation is accomplished using a blunt active electrode, a coag or high blend waveform, and relatively low power. The less concentrated current dries and shrinks the affected cells causing a deeper penetration of thermal modification to the cells than is accomplished using a blend mode during cutting or by fulguration.

Fulguration coagulation is accomplished using either a blunt or fine electrode with a coag mode waveform at high power. The active electrode is kept slightly spaced from the surface to be coagulated so that sparks jump across the gap. The surface area contacted by and the current from each spark is small so that the resulting thermal modification is shallow.

To avoid electrical shock to the patient caused by the depolarization of nerve or muscle cells by a non-physiologic electric voltage, frequencies above 300 kHz are used. To avoid electrical burns, the dispersive electrode must be carefully applied and care must be taken that the patient avoid metallic contacts. Further, the surgeon handling the active electrode must avoid applying it to his or her own body or touching it to any conductive tool or appliance.

The smoke produced during electrosurgery has an odor that is unpleasant, strong, and persistent. The smoke comprises organic gases, water vapor, visible and sub-visible solid particles, viruses, and virus particles. Although the infectious potential of viruses and virus DNA carried in the smoke plume has not been established clearly, it is generally considered good practice to remove the smoke from the surgical field and filter it to minimize this potential. In the past, smoke removal and filtering has required a separate non-integrated smoke evacuator appliance.

Typically, a patient with an abnormal smear obtained during a colposcopic examination is identified as a candidate for an electrosurgical excision procedure using a loop. At the beginning of the procedure, routine colposcopy is performed using acetic acid and iodine to outline the cervical lesion. The patient is anesthetized and the dispersive electrode is applied.

After the patient has been prepared as briefly set forth above, the loop is connected to the electrosurgical unit in a manner such that operation is controlled by a hand or foot control. When the hand or foot control is activated, power from the electrosurgical unit is supplied thereby activating the loop. Using a slight downward pressure, the loop is pushed into the cervical tissue perpendicular to the surface as deeply as needed. The loop is then advanced slowly across the cervix underneath the transformation zone and then withdrawn perpendicular to the surface of the cervix. The entire excision takes only about 5 to 10 seconds. The excised specimen is then removed for examination. After the excision, a diathermy ball operated at the coagulation mode is used to coagulate the cervical wound.

Electrosurgical excisions using a loop have several advantages over other procedures using a laser, cold knife, or cryogenic techniques. The tissue is removed rather than destroyed so that the entire transformation zone may be sent for histological examination. This minimizes the possibility of missing invasive disease. Additionally, the procedure may be performed at a patient's first visit to a colposcopy clinic, thereby affording valuable time savings to the patient and the colposcopy clinic.

In view of the marked advantages offered by the procedure for electrosurgical excision using a loop, the procedure is becoming more widely known and practiced. Consequently, practitioners who would have little or no use for an electrosurgical unit and/or a smoke evacuator are now beginning to find a need for such equipment. Heretofore, however, such equipment has not been designed to accommodate specifically the needs attendant to the LEEP and/or LLETZ procedures and there is no appliance available that provide both power for the electrosurgical tool and smoke evacuation. Moreover, since practitioners having less experience with these techniques are using them on their patients, safety features and convenience or ease of use are important factors.

One significant problem that is now being experienced during electrosurgery is the failure to evacuate the smoke plume created during the procedure. If the practitioner does not have a smoke evacuator available or if the practitioner merely forgets to turn it on, significant problems result. The smoke incident to electrosurgery can obscure the visual field, thereby increasing the chance that the practitioner will make an undesired cut or burn. Additionally, the odor of the smoke is unpleasant and pervasive. It is extremely difficult to remove the odor if it once contaminates the surgical environment. Although it is not confirmed, there is suspicion that the smoke plume may, in some instances, be infectious thereby endangering all that inhale the smoke.

Another significant problem occurs when the practitioner, although remembering to turn the smoke evacuator on, fails to turn it off when it is no longer needed. In such cases, the smoke evacuator make be left running for several minutes longer than is actually needed. This extraneous operation of the smoke evacuator substantially reduces the useful life of the filters and the evacuator motor, leading to expensive repairs, down time, or replacement.

Hence, it would be a substantial contribution to the art if an improved apparatus and method for driving an electrosurgical tool while simultaneously providing smoke evacuation could be provided. It would be a further advance in the art if the apparatus were provided in a single system designed to accommodate specifically the electrosurgical procedures known as LEEP and LLETZ. The present invention provides such an apparatus and method.

OBJECTS AND BRIEF SUMMARY OF THE INVENTION

In view of the foregoing needs and problems experienced by surgeons performing electrosurgery, it is a primary object of the present invention to provide an electrosurgical generator with integrated smoke evacuation capability.

It is another object of the present invention to provide an apparatus designed to accommodate specifically the electrosurgical procedures of LEEP and LLETZ.

A further object of the present invention is to provide an apparatus that automatically provides smoke evacuation upon the activation of the electrosurgical tool and a time-delayed automatic shut off of the smoke evacuation upon deactivating the electrosurgical tool.

Still another object of the present invention is to increase the useful life of the smoke evacuator filters and motor by eliminating extraneous operation of the filters and motor.

Yet another object of the present invention is to provide an electrosurgical generator with automatic smoke evacuation that is relatively inexpensive, safe and convenient to use, and will encourage practitioners to become knowledgeable and skilled in performing the LEEP and LLETZ procedures.

Another object of the present invention is to provide a combination smoke evacuation electrosurgical tool which positions the smoke evacuator tube in the close vicinity of the tool during electrosurgery, thereby providing immediate smoke evacuation and manipulation of the tool and tube with one hand.

The foregoing objects are accomplished by an apparatus of the present invention which provides both power to drive the electrosurgical tool and smoke evacuation in a single appliance that is convenient and safe to use.

One preferred embodiment of the present invention combines an electrosurgical power generator and a filtered smoke removal system into a single compact instrument comprising an electrosurgical generator module and a smoke removal module. The electrosurgical generator module is designed according to the same principles as larger general surgery units that are commonly used in hospital operating rooms; however, its power output is limited to the range necessary for the shallower and less extensive cuts made during LEEP or LLETZ procedures.

The smoke removal module is integrated with the electrosurgical generator module to enhance convenience and safety of the LEEP and LLETZ procedures. The smoke removal module is designed to remove smoke that would otherwise obscure the visual field during the procedure, to filter visible particles from the smoke, to absorb unpleasant odor, and to reduce the virus count in the filtered smoke plume to avoid spreading infection.

The smoke removal module comprises a first-stage prefilter, an activated charcoal filter, a particulate filter, and a vacuum assembly comprising a motor and impeller. The first-stage filter removes visible particles and most sub-visible particles, including viruses and virus-carrying aerosols. The activated charcoal filter removes the odorous gases. The particulate filter removes most organisms and sub-visible particles that may remain. The vacuum assembly creates the negative pressure and airflow necessary to draw the smoke from the surgical field and through the filters.

In the preferred embodiment, the first two filter stages are supplied as a disposable two-stage unit that may be easily changed and discarded. The third stage filter (the particulate filter) and the vacuum assembly are installed within the instrument housing. The third stage filter is removable from the housing for less frequent disposal.

The smoke removal module is turned on automatically by internal circuitry whenever the cut, blend or coag modes of the electrosurgical generator module are activated. The smoke removal module also automatically shuts off after a short time delay, e.g., two seconds, after the electrosurgical tool becomes inactive. In addition to the convenience to the practitioner, the intermittent operation is beneficial to the life of the filters and the vacuum motor.

In the preferred embodiment of the present invention, the controls utilize a digital display to show the predetermined selection of the power level in watts.

For additional convenience, the electrosurgical tool may be joined with the smoke evacuation tube, either in parallel or concentrically. This directs the suction of the smoke evacuator to the close vicinity of the surgical field and permits the practitioner to perform the electrosurgical procedures without concern about adequate smoke removal. The practitioner handles the electrosurgical tool and the smoke evacuation tool simultaneously in the same hand.

These and other objects and features of the present invention will become more fully apparent through the following description and appended claims taken in conjunction with the accompanying drawings.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Referring now specifically to the drawings, wherein like numerals indicate like parts throughout, the electrosurgical unit of the present invention is generally designated at 10. Electrosurgical unit 10 utilizes a digital display and combines an electrosurgical power supply to smoke evacuation in a manner particularly suitable for performing the electrosurgical procedures of LEEP and LLETZ, briefly described above. Electrosurgical unit 10 comprises an electrosurgical generator module, generally designated at 12, and a smoke removal module, generally designated at 14.

Figure 1:
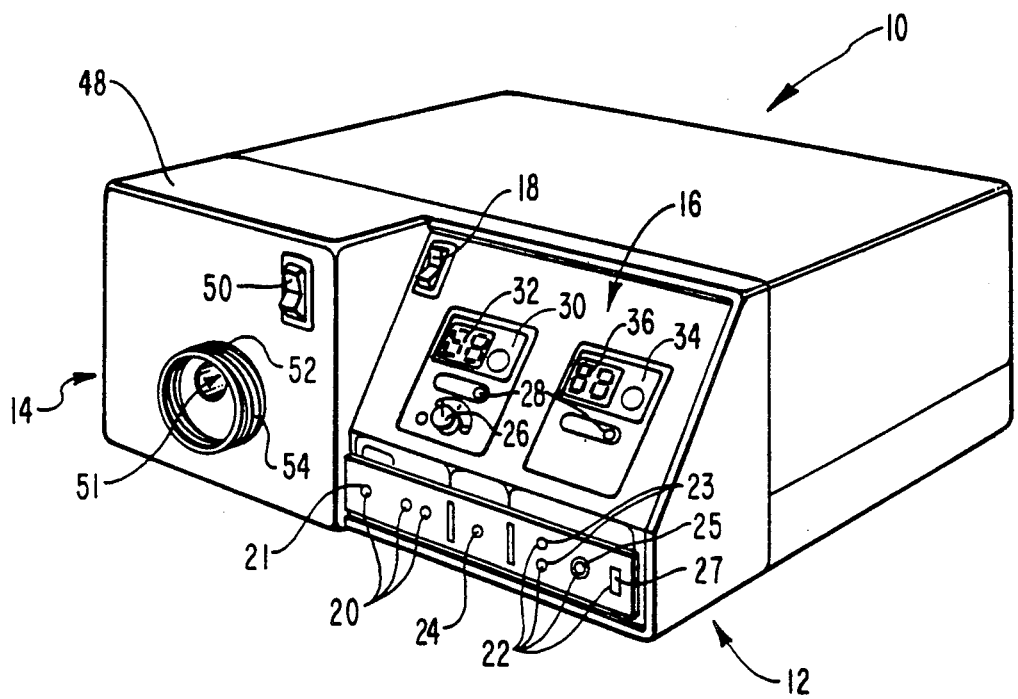
FIG. 1 is perspective view of the present invention showing a preferred control panel for the electrosurgical generator module and a vacuum port for the smoke removal module.

Referring now to FIG. 1, the electrosurgical generator module 12 comprises a control panel 16 having a power switch 18, handswitch jacks 20, dispersive electrode jacks 22, an alarm indicator 24, a mode select switch 26, power indicators 28, a cut/blend power control 30 with a cut/blend digital display 32, and a coag power control 34 with a coag digital display 36. Disposed on the back of the electrosurgical generator module 12, and therefore not shown, are a foot switch connector, audio volume adjust control, fuse sockets, and a power connector.

The power switch 18 is preferably a rocker switch used to turn the power to the electrosurgical unit 10 on or off. Power switch 18 must be turned on to enable all functions of the electrosurgical unit 10. Although other types of switches may be used, a rocker switch is preferred. One alternative switch contemplated is a push button on-off switch that can be illuminated when disposed in the "on" position.

Figure 2:
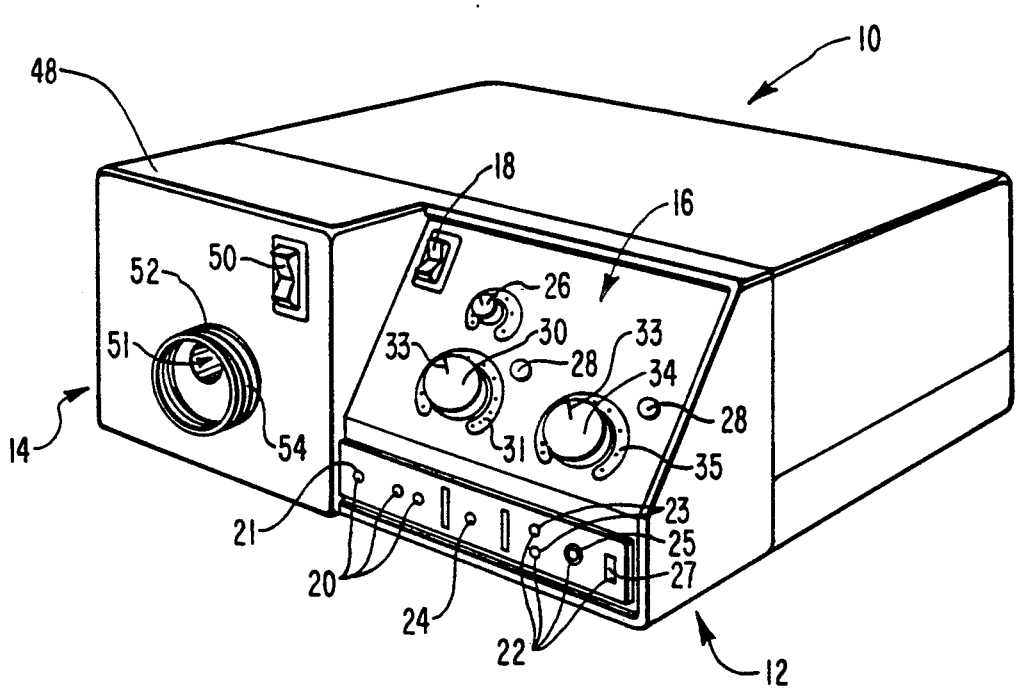
FIG. 2 is a perspective view of an alternative embodiment of the present invention showing another preferred control panel for the electrosurgical generator module and a vacuum port for the smoke removal module.

The control panel 16 has three monopolar handswitch jacks 20 in order to accommodate most of the reusable and disposable handswitch pencil holders that are presently available for use in electrosurgery. One of the handswitch jacks 20 is also designed to accommodate a non-switching holder for a monopolar electrosurgical tool. In FIGS. 1 and 2, this handswitch jack 20 also bears the reference number 21. When jack 21 is used with a non-switching holder, the power to the electrosurgical tool can be controlled using a footswitch connected to the footswitch connector on the back panel of the electrosurgical unit 10.

The preferred embodiment of the electrosurgical unit 10 has three sets of dispersive electrode jacks 22 to accommodate all of the dispersive pad cable configurations commonly available. A pair of jacks 23 are provided to take two redundant leads (see FIGS. 4A and 4B) to a dispersive electrode pad. If either of the leads has broken continuity, or if either lead is omitted, the alarm indicator 24 is activated (a light is illuminated and an audio signal sounds) and the current from the electrosurgical unit 10 is shut off automatically. As shown in FIGS. 1 and 2, the center dispersive electrode jack 22 is of the phone jack variety, also designated as phone jack 25, and is designed to accommodate phone plugs that are provided with many available dispersive electrode pads. Likewise, the rectangular dispersive electrode jack 22 is a rectangular socket 27 designed to be compatible with most of the remainder of dispersive electrode pads.

Alarm indicator 24 is a safety feature that illuminates whenever the electrosurgical unit 10 is disabled due to incomplete redundant dispersive electrode pad connections. Illumination of the alarm indicator 24 is accompanied by a distinct audio tone. The volume of the tone is regulated by the volume adjust control (not shown) disposed on the back of the electrosurgical unit.

To allow the practitioner to select the appropriate mix of cut and coagulation activity for the electrosurgical tool, the mode select switch 26 is provided. In the cut mode, a continuous alternating voltage is supplied to the electrosurgical tool. If the tool is sufficiently fine in its structure, it will cut through tissue very cleanly with little surface heating that would stop bleeding. In the blend modes, the same tool will cut through the tissue, but, concurrently, the surface of the cut will be heated to accomplish a degree of coagulation. Each successive blend mode provides successively larger degrees of coagulation. During typical operation, in switching between modes, the total power delivered to the electrosurgical tool is maintained approximately constant at the level selected by the cut/blend power control 30.

The cut/blend power control 30 is used to select the level of power supplied to the electrosurgical tool. With the preferred embodiment being described herein, the electrosurgical unit 10 is designed specifically for use during LEEP and LLETZ procedures having a maximum power output of 100 watts, approximately twice the power needed for LEEP and LLETZ procedures. For safety reasons, if there occurs an apparent power deficiency it is advisable to first verify that all electrical connections are in good order and that the patient dispersive electrode pad is applied properly before increasing the power to improve the cutting efficiency of the electrosurgical tool.

In general, higher power levels are required for thicker or blunt cutting electrodes or for deeper submersion of the cutting electrodes. Hence, although the preferred embodiment of the present invention has a maximum power output of approximately 100 watts, it should be understood that an electrosurgical unit 10 having a much higher power output is considered to be within the spirit and intended scope of the invention. Such higher powered electrosurgical units 10 could be used for electrosurgical procedures other than the LEEP and LLETZ procedures where it is also advisable to have smoke evacuation during the procedure.

If coagulation is desired, the coag power control 34 regulates the amount of power supplied to the electrosurgical tool. The amount of power being supplied appears on the coag digital display 36 in a manner similar to the display of power level on the cut/blend digital display 32. Generally, power of 50 watts will accomplish spray coagulation using a 5 mm or smaller ball electrode. Smaller or finer electrodes require less power. Low power settings are used to effect desiccation coagulation, while high power settings are used to effect fulguration coagulation. When the electrosurgical unit 10 is being operated in the coag mode, the power indicator 28 associated with the coag power control 34 is illuminated.

Figure 3:
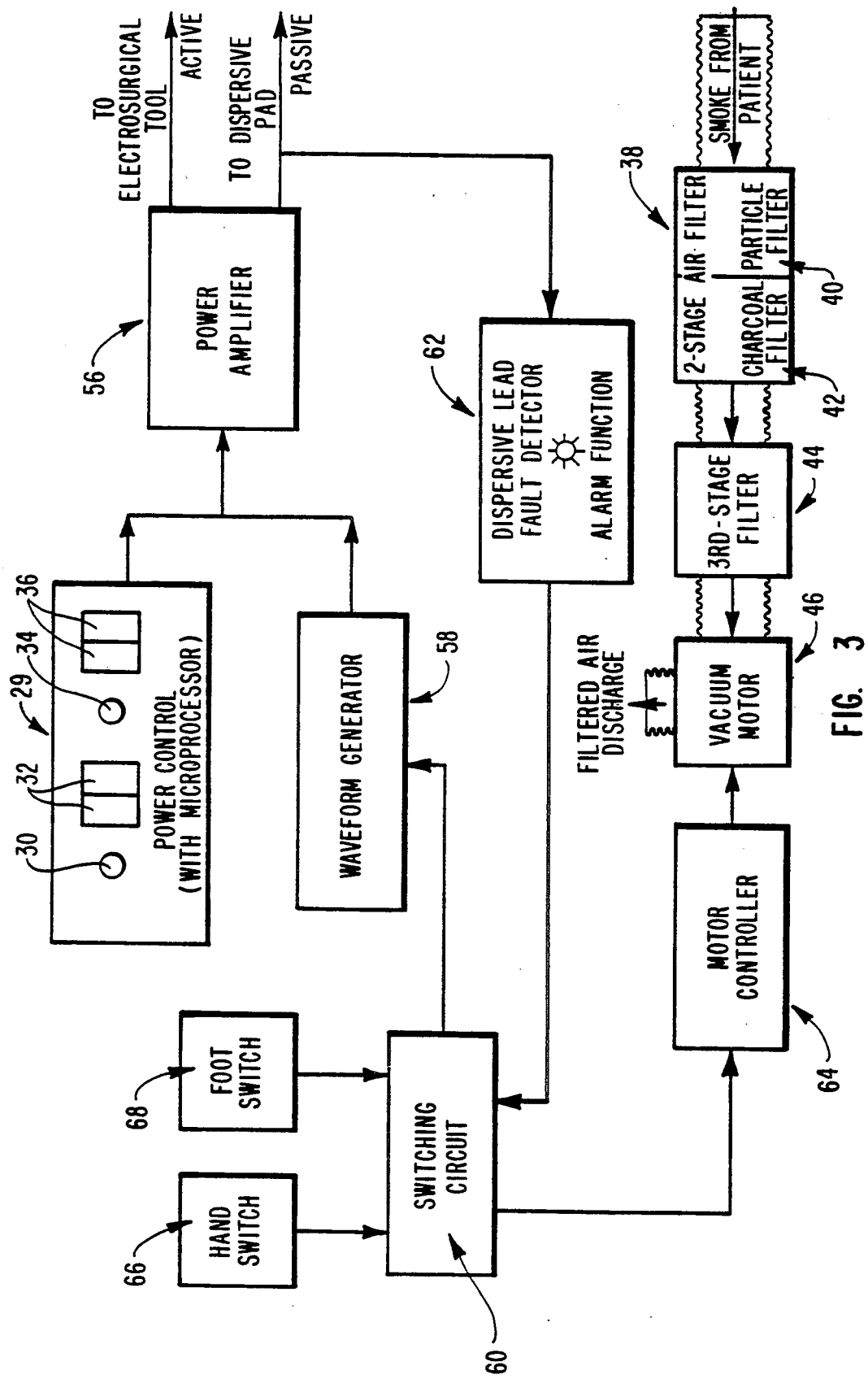
FIG. 3 is a block diagram of the present invention showing the various operational components and their interconnections.

The smoke removal module 14 is part of a smoke removal system, illustrated in block diagram in FIG. 3, comprising a two-stage air filter 38 with a first-stage prefilter 40 and an activated charcoal filter 42, a third-stage air filter 44, and a vacuum assembly comprising a vacuum motor 46 and impeller (not shown). The first-stage prefilter 40 removes visible particles and most sub-visible particles, including viruses and virus-carrying aerosols. The activated charcoal filter 42 removes the odorous gases. The third-stage air filter 44 is a particulate filter which removes most organisms and sub-visible particles that may remain. The vacuum assembly creates the negative pressure and airflow necessary to draw the smoke from the surgical field and through the filters.

In the preferred embodiment, the two-stage air filter 38 is a disposable unit that may be easily changed and discarded. The third-stage air filter 44 and the vacuum motor 46 and impeller are installed within an instrument housing 48. The third-stage air filter 44 is removable from the housing 48 for less frequent disposal. After use, the two-stage air filter 38 can be a source of odor and possible viral contamination. Also, using filter 38 through too many procedures may compromise the particle and odor removal efficiency. Hence, it is preferred that the two-stage air filter 38 be discarded daily or after thirty LEEP procedures if more than thirty procedures are performed in a single day. The internal third-stage air filter 44, being protected by the two-stage air filter 38, can withstand approximately 1000 times as many procedures as the two-stage filter 44. It is recommended that the third-stage air filter 44 be replaced annually.

Although other filters may be used, a two-staged air filter 38 in combination with the third-stage air filter 44 is preferred. A preferred type of filter combination includes a HEPA (high efficiency particulate) prefilter to remove solid particles, aerosols, and most virus size particles and a layer of activated charcoal to absorb odorous gases. Third-stage air filter is a particulate filter that serves to further reduce the virus count.

In an evaluation of this filter combination by filtering the smoke from over 100 cuts from beef hearts, there was no detectable odor in the outflow from the vacuum motor 46. Further, particle filtering was evaluated on particle sizes of 0.1, 0.3, and 0.5 microns. Individually, the first-stage prefilter 40 showed at least a filtering efficiency of 99.96% on all three particle sizes, while the third-stage air filter 44 showed at least a filtering efficiency of 99.98% for the same particle sizes. The combined efficiency of the two filters was at least 99.999% efficient. Although the diameter of the human papillomavirus is 0.055 microns, roughly half of the smallest particle size evaluated in the filter tests, it should be noted that these types of filters usually have poorest efficiencies at about 0.3 microns. Smaller particles, like viruses, are acted upon by Brownian motion to give them an effective cross section much larger than their diameter so that the filter efficiencies are believed to be equal to or better than those observed using larger particles.

Although an on-off switch may be provided, the smoke removal module 14 shown in FIGS. 1 and 2 does not have an on-off switch, but rather is turned on automatically by internal circuitry whenever the cut, blend or coag modes of the electrosurgical generator module 12 are activated. The smoke removal also automatically shuts off after a short time delay, e.g., two seconds, after the electrosurgical tool becomes inactive. This controlled intermittent operation is beneficial to the life of the filters 40, 42, and 44 and the vacuum motor 46.

Disposed on the housing is a vacuum level switch 50 which regulates whether the smoke removal module 14 operates at high speed or a low speed level. Like the power switch 18, it is preferred that the vacuum level switch be a rocker switch although other types of switches can be used.

At the low speed level the suction created is sufficient for removing smoke produced during the LEEP and LLETZ procedures, and the vacuum motor 46 runs quieter than during operation at the high speed level. In the preferred embodiment, operation of the smoke removal module 14 at the high speed level moves about forty percent (40%) more air than at the low speed level. Operation at the high speed level is particularly useful whenever the distal end of the smoke evacuator tube has a very small diameter or in the event that the smoke is not being completely removed at the low speed level.

The vacuum motor 46 preferred produces pressure reduction, at the low speed level, sufficient to draw approximately 80 liters of air per minute through a 15 cm long smoke evacuator tube having a 7 mm internal diameter. This rate has proved effective in removing smoke from the surgical field as required during the LLETZ procedure. A smaller diameter tube reduces the flow so that it may be necessary to use the high speed level with a smaller diameter tube. Further, when a LEEP procedure is used outside the vaginal cavity, smoke removal is more effective at the high speed level using a larger diameter smoke evacuation tube.

Housing 48 has a vacuum port 51 which is encircled by a filter connection collar 52. Air drawn by the vacuum assembly is drawn through vacuum port 51 into the third-stage air filter 44 within the housing 48. In a preferred embodiment, the filter connection collar 52 has threads 54 (see FIGS. 1 and 2) and the two-stage air filter 38 is configured to connect to the filter connection collar 52 in threaded engagement. In this manner, the two-stage air filter 38 can be removed for disposal and a new two-stage air filter can be replaced easily. In fact, it is preferred that the two-stage air filter 38 and the attached smoke evacuator hose be disposable.

An alternative preferred embodiment of the present invention is illustrated at FIG. 2. With this alternative embodiment, the cut/blend power control 30 and the coag power control 34 do not have digital displays 32 and 36. Rather, cut/blend power control 30 and coag power control 34 are knobs each having a power level scale 31 and 35, respectively, disposed adjacent thereto. As each knob is rotated to adjust the level of power, an indicator 33 on each knob indicates the power level selected from the respective power level scale 31 and 35.

Although the basic electrical circuitry that can be used to comprise the internal circuitry of the electrosurgical unit 10 of the present invention may vary according to various features provided and design choice, it should be understood that such variations are considered to be within the spirit and intended scope of the invention. Accordingly, reference is now made to FIG. 3 wherein the basic components of the electrosurgical unit 10 of the present invention are shown in block diagram relationship. Electrosurgical unit 10 further comprises a power control 29, a power amplifier 56, a waveform generator 58, a switching circuit 60, a dispersive lead fault detector 62 with alarm function, a motor controller 64, vacuum motor 46 with impeller, and the third-stage air filter 44. The arrows interconnecting various of the basic internal components indicate communication relationships between components.

Power control 29 communicates with the cut/blend power control 30 and the coag power control 32 and the respective digital displays 32 and 36. Preferably, power control 29 utilizes a microprocessor to process the power level and type of power selection made by the practitioner and to communicate that selection to the power amplifier 56.

Power amplifier 56 communicates with the handswitch jacks 20 and dispersive electrode jacks 22. A lead from one of the handswitch jacks 20 serves as the active lead and is connected to the electrosurgical tool. A lead from one of the dispersive electrode jacks 22 serves as the passive lead and is connected to the dispersive electrode pad applied to the patient. Power amplifier 56 also receives communication from the waveform generator 58.

The waveform generator 58 communicates with the mode selection switch 26 and generates the waveform corresponding to the practitioner's selection of the cut mode or a cut/blend mode of operation. The waveform generator then communicates that waveform to the power amplifier 56 which in turn transmits the appropriate waveform at the selected power level to the active lead and then on to the electrosurgical tool.

As described above, activation of the electrosurgical tool is controlled by either a hand switch 66 or a foot switch 68. In the case of hand switch 66 activation, the hand switch 66 is disposed on a reusable or disposable handswitch pencil holder of a type known in the art. This handswitch pencil holder is connected to the active lead and the electrosurgical tool is connected to the handswitch pencil holder so that the electrosurgical unit 10 communicates with the electrosurgical tool. Similarly, the foot switch 68 is connected to the electrosurgical unit 10 which in turn communicates with the electrosurgical tool.

To activate the electrosurgical tool, the hand switch 66 or the foot switch 68 is turned "on." This signals the switching circuit 60 to which the hand switch 66 or the foot switch 68 is connected. The switching circuit 60 in turn communicates such activation to the waveform generator 58 which communicates the activation to the power amplifier 56 which supplies the selected power and waveform to the active lead connected to the electrosurgical tool. Simultaneously, the switching circuit 60 communicates such activation to the motor controller 64 which activates the vacuum motor 46 so that the smoke removal function is activated simultaneous to the supply of power to the electrosurgical tool. Consequently, smoke can be drawn from the patient during the electrosurgical procedure through both the two-stage air filter 38 and the third-stage air filter 44 into the vacuum assembly.

To deactivate the electrosurgical tool, the hand switch 66 or the foot switch 68 is turned "off." This signals the switching circuit 60 to which the hand switch 66 or the foot switch 68 is connected. The switching circuit 60 in turn communicates such deactivation to the waveform generator 58 which communicates the deactivation to the power amplifier 56 which discontinues supplying the selected power and waveform to the active lead connected to the electrosurgical tool. Simultaneously, the switching circuit 60 communicates such deactivation to the motor controller 64 which provides a time delay before it deactivates the vacuum motor 46 so that the smoke removal function is deactivated.

In the event that the return of power via the passive lead to the power amplifier 56 is interrupted or continuity is broken in the redundant leads to the dispersive electrode pad, such is detected by the dispersive lead fault detector 62 which activates the alarm function, thereby illuminating the alarm indicator 24, sounding the audio alarm tone, and communicating the fault to the switching circuit 60. The switching circuit 60 then deactivates the electrosurgical tool immediately.

Figure 4A:
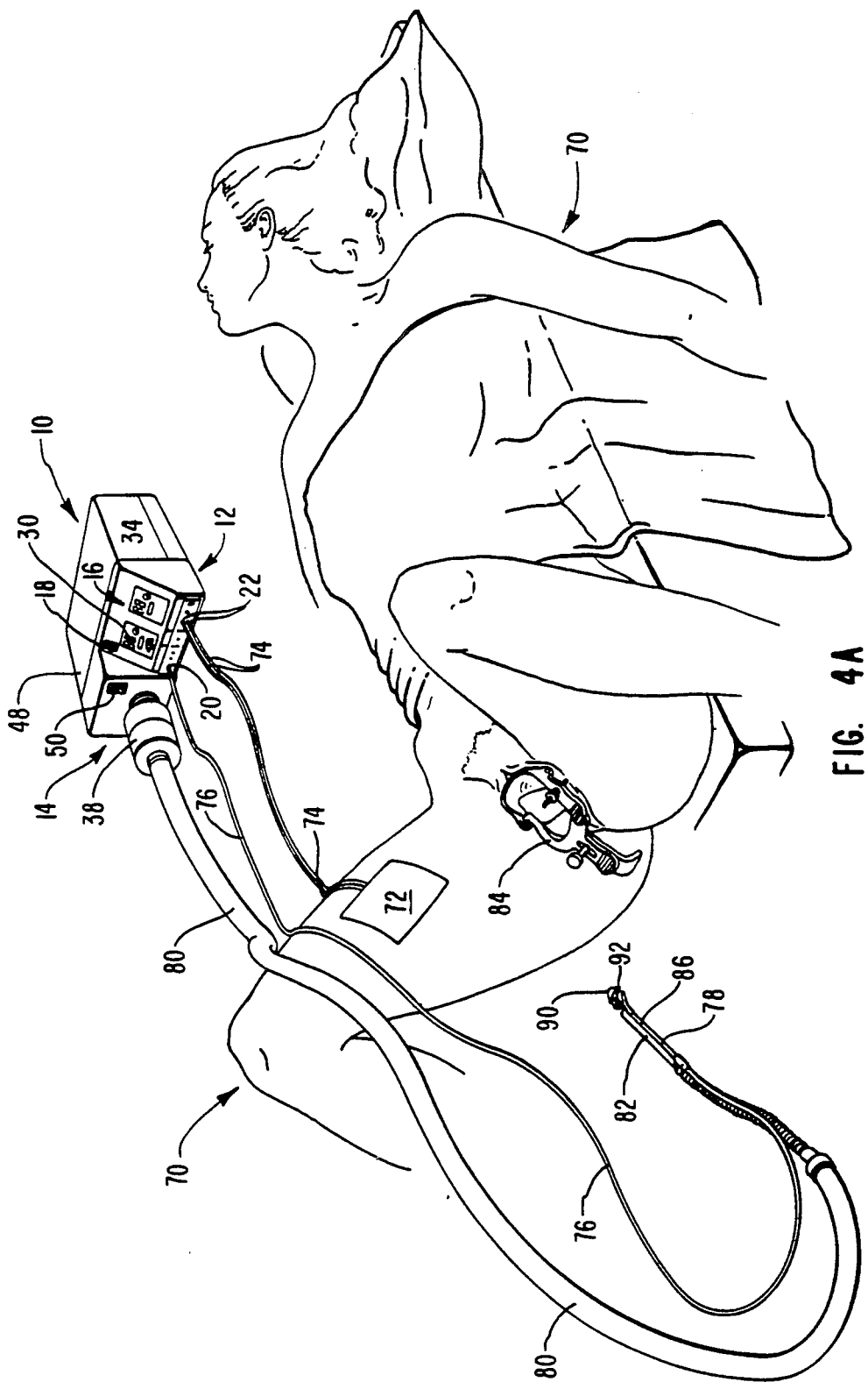
FIG. 4A is a perspective view of the electrosurgical environment showing an electrosurgical unit of the present invention connected to a patient and a preferred embodiment of the electrosurgical tool joined with the smoke evacuator tube.
Figure 4B:
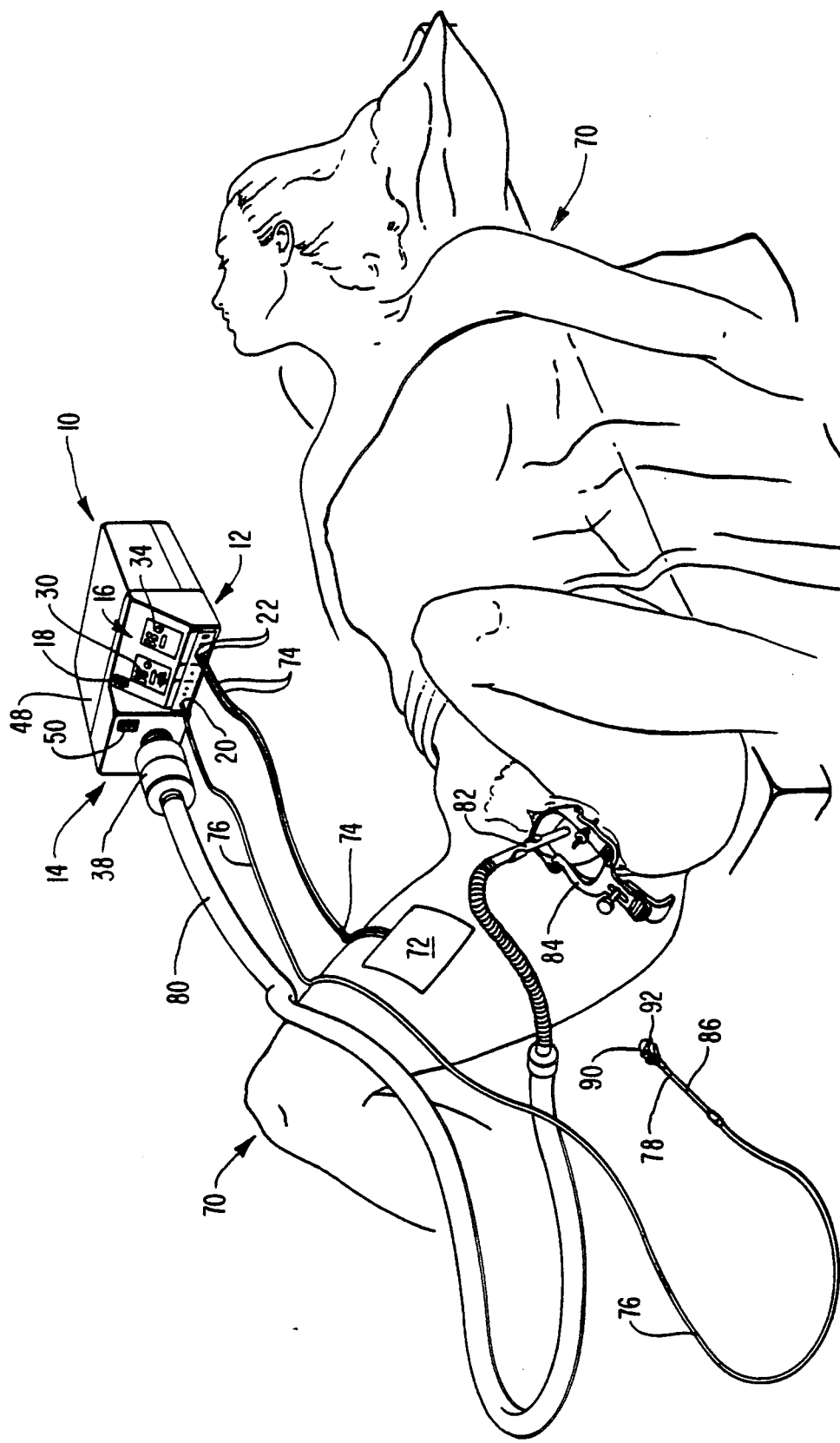
FIG. 4B is a perspective view of the electrosurgical environment showing an electrosurgical unit of the present invention connected to a patient with the smoke evacuator tube connected to the speculum that is inserted into the patient's vagina.

Operation of the electrosurgical unit 10 of the present invention is shown in the surgical environment in FIGS. 4A and 4B. In FIG. 4A, a patient 70 has been prepared for the electrosurgical procedure by securing a dispersive electrode pad 72 to the patient's thigh and connecting the redundant passive leads 74 which are connected to the dispersive electrode pad 72 to the electrosurgical unit 10. An active lead 76 is connected to the electrosurgical unit 10 and to an electrosurgical tool 78. The electrosurgical tool 78 shown is of the type shown with more particularity in FIG. 5. Extending from and connected to the two-stage air filter 38 is a smoke evacuation hose 80. Smoke evacuation hose 80 is in turn connected to a smoke evacuator tube 82. With the preferred embodiment shown in FIG. 4A, the electrosurgical tool 78 and the smoke evacuator tube 82 are joined to combine their respective features into a single instrument.

Once the patient 70 is prepared essentially as shown, the electrosurgical procedure can commence. A routine colposcopy is performed using acetic acid and iodine to outline the cervical lesion and the patient 70 is anesthetized. The power switch 18 for the electrosurgical unit 10 is turned "on" and the power level is selected, as is the mode of operation whether it be a pure cut, a blend, or a coag mode. Thereafter, when hand switch 66 or foot switch 68 is activated, power from the electrosurgical unit 10 is supplied thereby activating the electrosurgical tool 78. Simultaneously, the smoke removal system is activated and the smoke evacuator tube 82 begins to draw air.

To perform an cervical excision using a loop electrosurgical tool 78 a slight downward pressure is applied, the loop is pushed into the cervical tissue perpendicular to the surface as deeply as needed. The loop is then advanced slowly across the cervix underneath the transformation zone and then withdrawn perpendicular to the surface of the cervix. The entire excision takes only about 5 to 10 seconds and the smoke created by the excision is removed continuously during the procedure. After a short delay following the deactivation of the electrosurgical tool 78, the smoke removal system shuts off automatically. The excised specimen is then removed for examination. After the excision, a diathermy ball can be connected to the active lead 76 and operated at the coagulation mode to coagulate the cervical wound while the smoke removal system again extracts the smoke created.

Turning now to FIG. 4B, an alternative mode of operation is illustrated. The patient 70 is prepared in the same manner as described above with the exception that a combined smoke evacuator tube 82 and electrosurgical tool 78 is not used. Instead, the smoke evacuator tube 82 is separate from the electrosurgical tool 78 and is removably connected to a speculum 84 which is inserted into the vagina of the patient 70. This disposes the smoke evacuator tube 82 in a position where it can draw air and, during the excision and subsequent coagulation, smoke from the vaginal cavity for filtering and odor removal.

Figure 5:
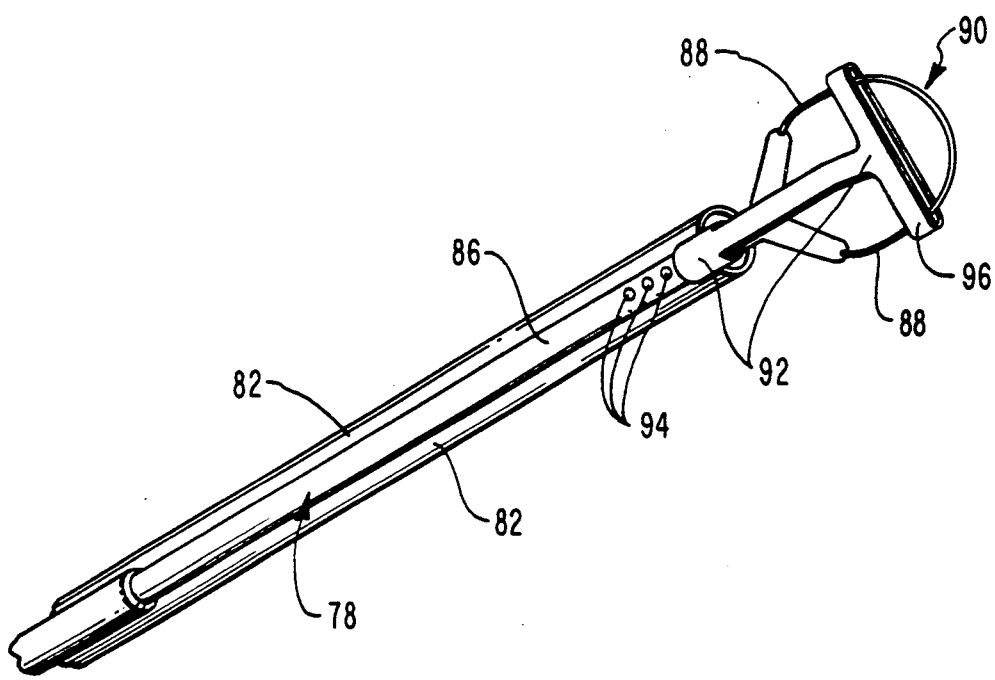
FIG. 5 is a perspective view of a preferred electrosurgical tool joined in parallel with the smoke evacuator tube.
Figure 6:
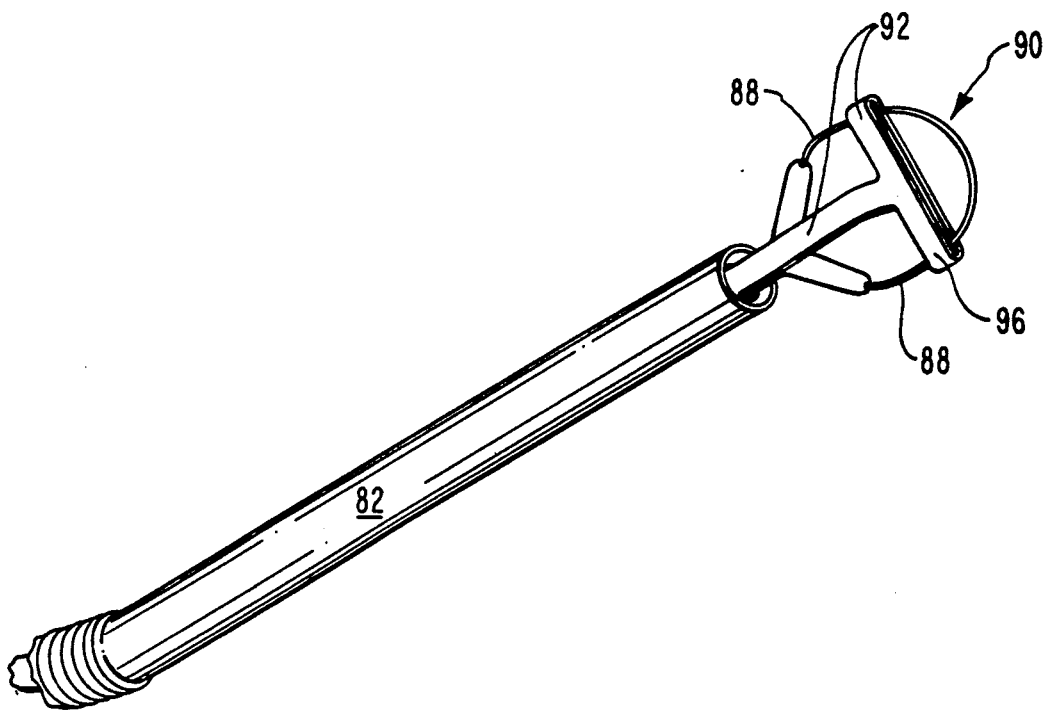
FIG. 6 is a perspective view of another preferred electrosurgical tool disposed concentrically within the smoke evacuator tube

FIGS. 5 and 6 illustrate examples of electrosurgical tools 78 combining electrosurgery capability with simultaneous smoke evacuation. FIG. 5 shows a parallel embodiment, while FIG. 6 shows a concentric embodiment. In both FIGS. 5 and 6 the electrosurgical tool 78 illustrated is an electrosurgical loop having an insulated shaft 86 with an extending thin wire 88 formed into a wire loop 90 at the distal end of the insulated shaft 86. Disposed on the insulated shaft 86 in slidable engagement is a depth gauge 92 which may be positioned according to markings 94 on the insulated shaft 86 to position a cross bar 96 of the depth gauge 92 to permit an excision of a predetermined depth as selected by the practitioner. With each of the configurations shown, the end of the smoke evacuator tube 82 is disposed not to obscure the practitioner's vision and adjacent the point of excision or coagulation for effective smoke removal. Also, due to the relatively small body of each combined tool, the practitioner may manipulate the tool as desired easily.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for operating an electrosurgical tool during electrosurgery, comprising:
a generator means for providing power to the electrosurgical tool;
a smoke removal means for removing and filtering smoke from the site of the electrosurgery; and,
a switching means for activating said smoke removal means substantially simultaneous to the activation of the electrosurgical tool by said generator means, such that said smoke removal means is activated automatically whenever the electrosurgical tool is activated.

2. An apparatus as set forth in claim 1, wherein said generator means comprises a power level selection means for setting the power within a range of power levels, whereby the level of power supplied to the electrosurgical tool is determined prior to activating the electrosurgical tool by selecting a setting corresponding to the level of power desired.

3. An apparatus as set forth in claim 2, wherein said generator means further comprises a display for displaying visually the level of power selected.

4. An apparatus as set forth in claim 3, wherein said display is digital.

5. An apparatus as set forth in claim 2, wherein the range of power levels available for selection has a maximum of 100 watts.

6. An apparatus as set forth in claim 1, wherein said generator means comprises a mode selection means for setting the mode of operation of the electrosurgical tool from among a plurality of modes of operation, whereby the mode of operation of the electrosurgical tool is determined prior to activating the electrosurgical tool by selecting a setting corresponding to the mode of operation desired.

7. An apparatus as set forth in claim 6, wherein one of said modes of operation is a cutting mode whereby the power supplied to the electrosurgical tool is supplied in a continuous, unmodulated waveform.

8. An apparatus as set forth in claim 6, wherein at least one of said modes of operation is a blend mode whereby the power supplied to the electrosurgical tool is supplied in a modulated waveform.

9. An apparatus as set forth in claim 1, wherein said generator means has a plurality of active lead jacks for accommodating various types of electrosurgical tool leads.

10. An apparatus as set forth in claim 9, wherein said generator means further comprises a hand switch and at least one of the active lead jacks is responsive to said hand switch for activating and deactivating the electrosurgical tool.

11. An apparatus as set forth in claim 9, wherein said generator means further comprises a foot switch and at least one of the active lead jacks is responsive to said foot switch for activating and deactivating the electrosurgical tool.

12. An apparatus as set forth in claim 1, wherein said generator means has a plurality of passive lead jacks for accommodating various types of dispersive electrode leads.

13. An apparatus as set forth in claim 1, wherein said generator means comprises a dispersive lead fault detector for detecting a break in the continuity of the power returning to the generator means, said dispersive lead fault detector activates an alarm means which provides a signal in the even a break in the continuity of the power is detected.

14. An apparatus as set forth in claim 1, wherein said smoke removal means comprises a vacuum means which draws air by suction and a plurality of filters.

15. An apparatus as set forth in claim 14, wherein at least one of said filters is a two-stage filter.

16. An apparatus as set forth in claim 15, wherein one of the stages of said two-stage filter comprises a particulate filter.

17. An apparatus as set forth in claim 15, wherein one of the stages of said two-stage filter comprises an activated charcoal filter.

18. An apparatus as set forth in claim 15, wherein said two-stage filter is disposable.

19. An apparatus as set forth in claim 15, wherein said two-stage filter is a HEPA filter.

20. An apparatus as set forth in claim 15 further comprising a housing for said vacuum means and said two-stage filter is connected to said housing in threaded engagement.

21. An apparatus as set forth in claim 14, wherein at least one of said filters is a third-stage particulate filter.

22. An apparatus as set forth in claim 21, wherein said third-stage particulate filter is replaceable.

23. An apparatus as set forth in claim 1, wherein said switching means comprises a delay means for delaying deactivation of said smoke removal means for a predetermined amount of time after the electrosurgical tool has been deactivated.

24. An system for performing electrosurgery, comprising:
an electrosurgical tool;
a generator means for providing power to said electrosurgical tool at a predetermined level;
a smoke removal means for removing and filtering smoke from the site of the electrosurgery, said smoke removal means comprising a smoke evacuator tube connected to said electrosurgical tool; and,
a switching means for activating said smoke removal means substantially simultaneous to the activation of said electrosurgical tool by said generator means, such that said smoke removal means is activated automatically whenever said electrosurgical tool is activated.

25. A system as set forth in claim 24, wherein said switching means comprises a delay means for delaying deactivation of said smoke removal means for a predetermined amount of time after the electrosurgical tool has been deactivated.

26. A system as set forth in claim 24, wherein said smoke evacuator tube is connected to said electrosurgical tool in parallel disposition.

27. A system as set forth in claim 24, wherein said electrosurgical tool is connected to said smoke evacuator tube in concentric disposition.

28. A system as set forth in claim 24, wherein said electrosurgical tool is an electrosurgical loop comprising a shaft with a proximal end and a distal end, said shaft having a wire loop disposed on the distal end of said shaft.

29. A system as set forth in claim 28, wherein said electrosurgical loop further comprises a depth gauge disposed in slidable engagement with said electrosurgical loop, whereby the amount of the wire loop exposed for making an electrosurgical excision is predetermined by sliding said depth gauge along the electrosurgical loop.

30. An apparatus capable of electrical connection to an electrosurgical unit and air flow connection to a smoke removal system for performing electrosurgery and evacuating smoke resulting from the electrosurgery, comprising:
an electrosurgical tool comprising an electrosurgical loop having a shaft with a proximal end and a distal end, said shaft having a wire loop disposed on the distal end of said shaft;
a depth gauge disposed in slidable engagement with said electrosurgical loop, whereby the amount of said wire loop exposed for making an electrosurgical excision is predetermined by sliding said depth gauge along said electrosurgical loop; and
a smoke evacuator tube connected to said electrosurgical tool.

* * * * *